(12) United States Patent
Jin

(10) Patent No.: US 9,308,385 B2
(45) Date of Patent: Apr. 12, 2016

(54) RTMS AT HARMONICS OF BIOLOGICAL SIGNALS

(71) Applicant: Newport Brain Research Laboratory Inc., Newport Beach, CA (US)

(72) Inventor: Yi Jin, Irvine, CA (US)

(73) Assignee: KOSIVANA HOLDINGS LIMITED, Limassol (CY)

( * ) Notice: Subject to any disclaimer, the term of this patent is extended or adjusted under 35 U.S.C. 154(b) by 269 days.

(21) Appl. No.: 13/858,693

(22) Filed: Apr. 8, 2013

(65) Prior Publication Data

US 2013/0267760 A1 Oct. 10, 2013

Related U.S. Application Data

(60) Provisional application No. 61/621,423, filed on Apr. 6, 2012.

(51) Int. Cl.
*A61N 2/00* (2006.01)
*A61B 5/00* (2006.01)
*A61B 5/0245* (2006.01)
*A61B 5/048* (2006.01)

(52) U.S. Cl.
CPC .............. *A61N 2/004* (2013.01); *A61B 5/0245* (2013.01); *A61B 5/048* (2013.01); *A61B 5/7282* (2013.01); *A61B 5/7257* (2013.01)

(58) Field of Classification Search
CPC ............ A61N 2/00; A61N 2/004; A61N 2/02
USPC ........................................ 600/9–15, 544–545
See application file for complete search history.

(56) References Cited

U.S. PATENT DOCUMENTS

| | | | |
|---|---|---|---|
| 5,769,778 A | 6/1998 | Abrams et al. | |
| 6,117,066 A | 9/2000 | Abrams et al. | |
| 7,976,451 B2 * | 7/2011 | Zangen et al. | 600/13 |
| 8,052,591 B2 * | 11/2011 | Mishelevich et al. | 600/14 |
| 8,303,480 B2 | 11/2012 | Rohan et al. | |
| 8,465,408 B2 | 6/2013 | Phillips et al. | |
| 8,475,354 B2 | 7/2013 | Phillips et al. | |
| 8,480,554 B2 | 7/2013 | Phillips et al. | |
| 8,585,568 B2 | 11/2013 | Phillips et al. | |
| 8,870,737 B2 | 10/2014 | Phillips et al. | |
| 8,888,672 B2 | 11/2014 | Phillips et al. | |
| 8,888,673 B2 | 11/2014 | Phillips et al. | |
| 8,926,490 B2 | 1/2015 | Phillips et al. | |
| 8,961,386 B2 | 2/2015 | Phillips et al. | |
| 2004/0077921 A1 | 4/2004 | Becker et al. | |
| 2008/0200749 A1 | 8/2008 | Zheng et al. | |
| 2009/0082690 A1 | 3/2009 | Phillips et al. | |
| 2010/0113959 A1 * | 5/2010 | Pascual-Leone et al. | 600/544 |

* cited by examiner

*Primary Examiner* — John Lacyk
(74) *Attorney, Agent, or Firm* — Saliwanchik, Lloyd & Eisenschenk

(57) ABSTRACT

Repetitive Transcranial Magnetic Stimulation (rTMS) is administered at a pulse rate that is equal to or a harmonic of a biological metric of a patient. The purpose is to provide frequency coupling among different organs (e.g., heart, brain, breathing, and gastrointestinal movement) through rhythmic entrainment. The specific harmonic chosen is the one closest to a desired EEG frequency. The desired EEG frequency is chosen based on the cognitive element or symptom that is targeted.

11 Claims, 2 Drawing Sheets

RTMS AT HARMONICS OF BIOLOGICAL SIGNALS

CROSS-REFERENCE TO RELATED APPLICATIONS

The present application claims priority under 35 U.S.C. §119(e) to U.S. Provisional Application No. 61/621,423, filed on Apr. 6, 2012, the disclosure of which is incorporated herein by reference in its entirety.

FIELD OF THE INVENTION

The present invention relates to methods of modulating brain activity with repetitive transcranial magnetic stimulation (rTMS) wherein the rTMS is administered at a frequency of a biological metric or a harmonic of a biological metric.

BACKGROUND OF THE INVENTION

Transcranial magnetic stimulation and rTMS have been used to treat many psychological and medical disorders such as major depressive disorder, Parkinson's disease, Alzheimer's disease, autism spectrum disorder (ASD), schizophrenia and others. Recently, Jin and Phillips, in US Patent Publication 2009/0082690, have disclosed a treatment protocol using rTMS where the output of the magnetic field is adjusted based on a patient's EEG intrinsic frequencies in an attempt to alter the patient's intrinsic EEG frequencies.

SUMMARY OF THE INVENTION

Briefly, in accordance with the present invention the brain activity of a mammal is modulated by subjecting the mammal to repetitive transcranial magnetic stimulation (rTMS) at a frequency of a biological metric, or a harmonic (including sub-harmonics) of the biological metric for a time sufficient to modulate the brain activity of the mammal. An improvement in a physiological condition, psychological condition, or a neuropsychiatric condition exhibited by the mammal is achieved. The biological metric can be any biological metric including but not limited to heart rate, respiratory rate, gastrointestinal movement rate, or an EEG frequency. Preferably, the brain activity to be modulated is a desired EEG band, such as, for example, the brains' alpha waves, and the rTMS frequency is equal to, or a harmonic or sub-harmonic of, a non-EEG biological metric that is closest to the targeted frequency in a desired EEG band such as for example the heart rate, which is a sub-harmonic of the alpha frequency. Other biological metrics include the patient's respiratory rate and the gastrointestinal movement rate (rate of peristalsis). Other EEG frequencies include the delta band (<4 Hz), the theta band (4-8 Hz), the beta band (13-30 Hz), the gamma band (~40 Hz) or the Mu band (8-13 Hz).

By modulating the brain activity of a mammal, improvements in physical conditions, psychological conditions, and neuropsychiatric conditions are improved in a non-invasive manner and usually without the need for medications. Physical conditions that can be improved include pain relief (pain management), blood pressure, stress, libido, motor function, physical performance, height (in children) or weight. Psychological conditions that can be improved included concentration/focus, sleep, alertness, memory, speech, intelligence, and other cognitive functions. Neuropsychiatric conditions that can be improved include symptoms of Autism Spectrum Disorder (ASD), Alzheimer's disease, attention deficit hyperactivity disorder (ADHD), schizophrenia, anxiety, depression, coma, Parkinson's disease, substance abuse, bipolar disorder, a sleep disorder, an eating disorder, tinnitus, traumatic brain injury, post traumatic stress disorder (PTSD), or fibromyalgia.

Of particular interest in the practice of the present invention are methods of modulating a human patient's alpha brain waves in a patient with ASD, chronic pain or Alzheimer's disease. The rTMS treatment protocol will begin as a daily regimen of 30 minutes of rTMS set at a frequency which is a harmonic of the patient's heart rate which is closest to the frequency in the alpha brain wave range of 8-13 Hz. As seen in Example 1 below, if the patient's heart rate is 1.5 Hz then the $6^{th}$ harmonic will be set a treatment frequency of the rTMS device at 9 Hz where his alpha EEG frequency may be at 9.1 Hz or 8.9 Hz. Each patient will vary depending on his/her specific biological measurements.

DETAILED DESCRIPTION OF THE INVENTION

The term "mammal" when used herein includes any mammal especially humans. Non-human mammals include non-human primates, zoo animals, companion animals (dogs, cats), performance mammals such as race horse and breeding animals.

Various bodily functions operate at frequencies that are harmonics or sub-harmonics of the brain's intrinsic frequency. For example, the heart rate is approximately the $6^{th}$, 7th, $8^{th}$, or $9^{th}$ sub-harmonic of the brain's alpha frequency at awake and the $2^{nd}$ or $3^{rd}$ sub-harmonic of delta at sleep. The breathing rate is generally the $5^{th}$ sub-harmonic of the heartbeat. The gastrointestinal movement frequency is approximately the $4^{th}$ or $5^{th}$ sub-harmonic of the breathing rate.

It is evident that it is advantageous for there to be coherence between the peak frequency of a dominant EEG activity and the nearest higher harmonic of a biological metric such as for example the resting heart rate. In various disease states coherence is low while in healthy states coherence is high. In a preferred embodiment of the present invention the frequency of an administered rTMS treatment is chosen according to the EEG peak frequency that has the highest coherence coefficient with the EEG.

Figure 1:
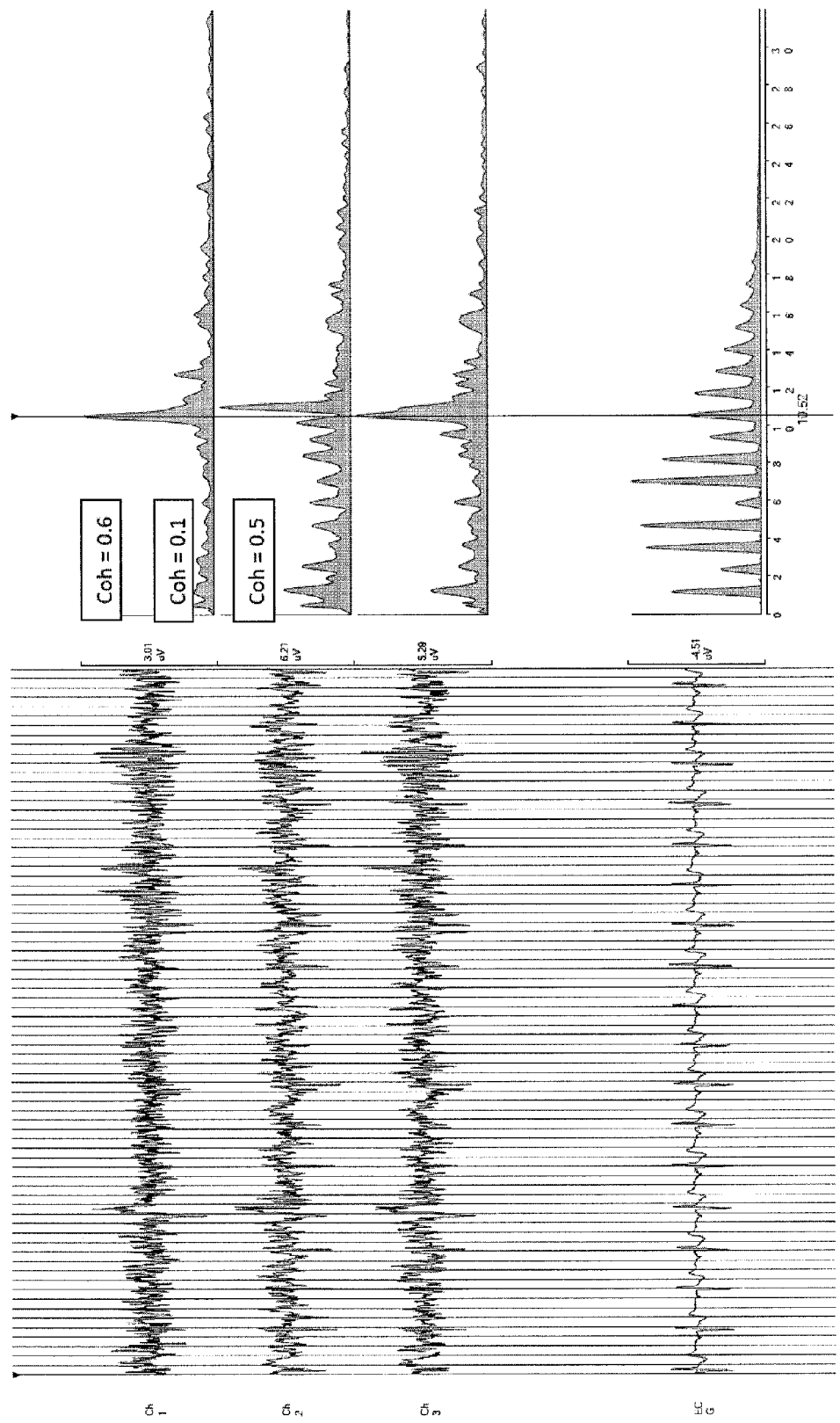
FIG. 1 shows coherence between the alpha band and the heart rate.

FIG. 1 shows a patient's alpha band EEG pattern in the upper left portion (top 3 patterns) with a corresponding fast Fourier transform (FFT) appearing to the right of each pattern showing frequency peaks. The bottom left pattern is an electrocardiogram (ECG) pattern of the same patient with the corresponding higher harmonics appearing to the right of the ECG pattern. The coherence coefficient is shown in a box to the right side of the EEG graphs. The highest coherence coefficient of the alpha peak frequency with the $9^{th}$ harmonic of the heart rate can be seen from the top EEG pattern (Coh=0.6). The $9^{th}$ harmonic of the heart rate is 10.52 Hz and this is the preferred frequency for this patient's rTMS treatment for conditions such as chronic pain, ASD and Alzheimer's disease.

Figure 2:
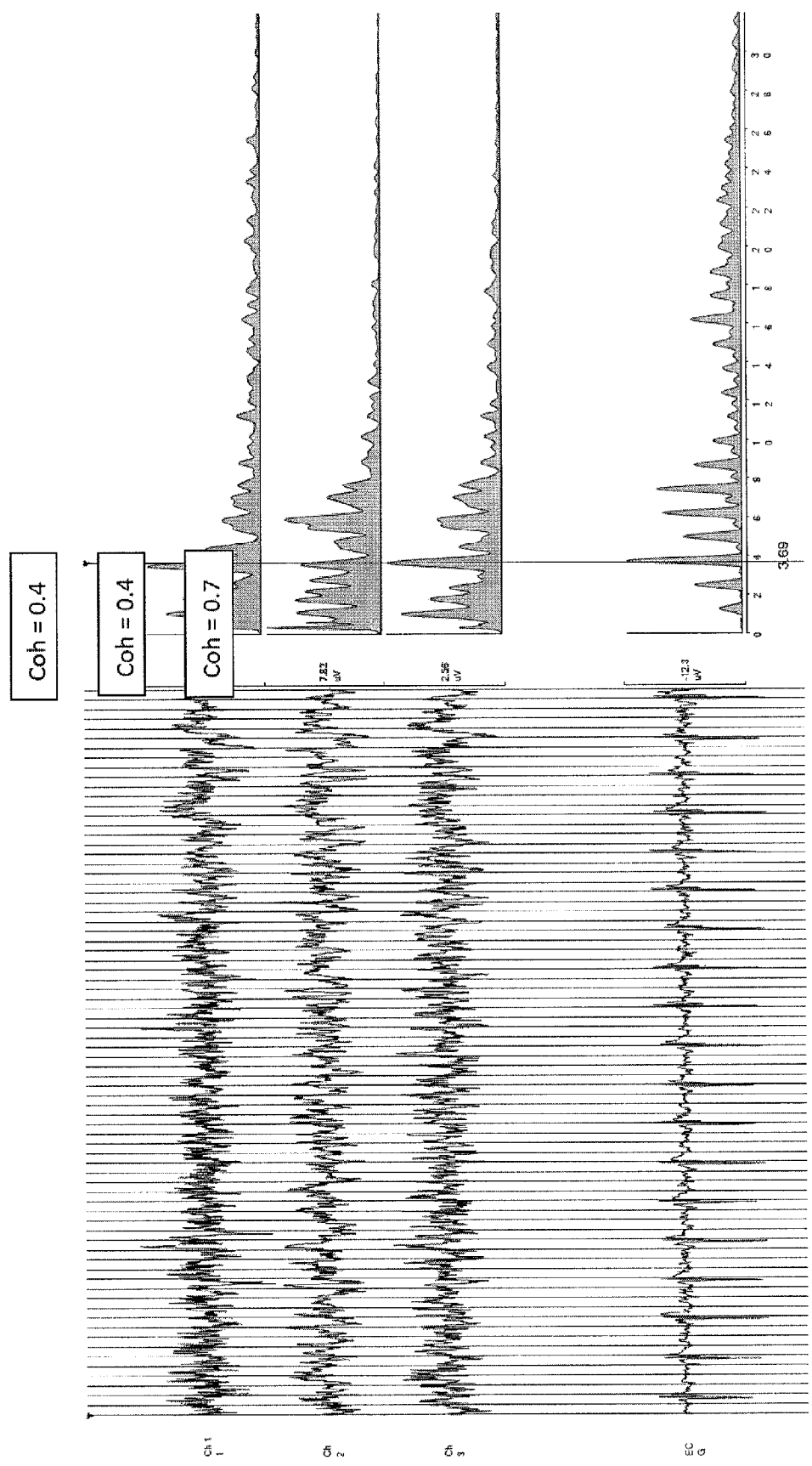
FIG. 2 shows coherence between the delta band and the heart rate.

FIG. 2 shows a patient's delta band EEG pattern in the upper left portion (top 3 patterns) with a corresponding fast Fourier transform (FFT) appearing to the right of each pattern showing frequency peaks. The bottom left pattern is an electrocardiogram (ECG) pattern of the same patient with the corresponding higher harmonics appearing to the right of the ECG pattern. The coherence coefficient is shown in a box to the right side of the EEG graphs. The highest coherence coefficient of the delta band peak frequency with the $3^{rd}$ harmonic of the heart rate can be seen from the bottom EEG pattern (Coh=0.7). The 3rd harmonic of the heart rate is 3.69 Hz and this is the preferred frequency for this patient's rTMS treatment for conditions such as insomnia and attention deficit disorders.

A desynchronized oscillatory system amongst the organs is less energy efficient. The frequency coupling among different organs develops by rhythmic entrainment in order to lower the total energy cost and increase efficiency of the system as a whole. Patients with various mental disorders are often found to have frequency "decoupling" between critical organs, such as heart and brain. Providing rTMS at the frequency (or a harmonic thereof) of one of these biological signals can make use of the body's natural resonance to influence brain activity and resynchronize the heart/brain/respiratory/gastro oscillation, lower energy, and increase efficiency and stability. This in turn will lessen the symptoms of the disorder or improve a physical condition which, in the case of Alzheimer's disease and ASD, results in improved cognitive function and motor function associated with movement or speech. Additionally, in underdeveloped children rTMS treatments according to the present invention may increase the height and weight of the treated child. In another embodiment of the present invention, chronic pain relief can be achieved by administering rTMS to a patient in chronic pain at a frequency that is a harmonic of the patient's heart rate preferably the $6^{th}$-$10^{th}$ harmonic of the heart rate.

By providing rTMS stimulation to the brain at a harmonic of the heartbeat, breathing rate, or gastrointestinal frequency, entrainment and the resonant property of the mammalian system will gradually improve the frequency coupling among organs. The brain is targeted because it is the central control mechanism for all organs in the body. The frequency chosen is preferably a harmonic of the heartbeat that is closest to an interested frequency that may be associated with the disorder, symptom, cognitive characteristic or physical condition of interest. Frequencies of interest include the following:

a. Delta band intrinsic frequency (<4 Hz). Delta waves are normally prevalent in infants, during slow wave sleep or during continuous attention tasks in adults. In pathological conditions, it is often associated with metabolic encephalopathy or other types diffused brain lesions. In general, rTMS at $2^{nd}$ or $3^{rd}$ harmonic of heartbeat are used to treat insomnia and improve attention.

b. Theta band intrinsic frequency (4-8 Hz). Theta waves are commonly found in children and during periods of drowsiness in adults. It is also associated with inhibition of elicited responses. It has been observed in pathological conditions such as focal subcortical lesions, metabolic encephalopathy, and deep midline disorders. In general, rTMS at $4^{th}$ or $5^{th}$ harmonic of heartbeat may help control impulsive behavior in autism and many other mental disorders c. Alpha band intrinsic frequency (8-13 Hz). Alpha band is normally found during periods of relaxation while closing the eyes. Physiologically it is associated with the process of inhibition control. Lack of alpha activity is found in autism, and other mental disorders, such as anxiety, schizophrenia, and ADHD. Reduced alpha frequency coherence has been found in patients with Alzheimer's disease. Excessive alpha activity may be seen in comatose conditions. In general, rTMS in this range will help treat autism, reduce anxiety, increase attention, or treat schizophrenia and Alzheimer's.

d. Beta band intrinsic frequency (13-30 Hz). Beta band is associated with alertness, busy or anxious thinking. Significant reduction of beta activity is often found in subjects treated with benzodiazepines. rTMS in this range will help to increase alertness.

e. Gamma band intrinsic frequency (~40 Hz). Gamma activity displays during cross-modal sensory processing or short term memory matching of recognized objects, sounds, or tactile sensations. A decrease in gamma band activity may be associated with cognitive decline, such as Alzheimer's disease. rTMS in this range is used to treat cognitive deficits in Alzheimer's disease or other forms of dementia.

f. Mu activity (8-13 Hz). Mu rhythm has frequency overlap with alpha wave but, instead of parietal occipital regions, it is only seen in the sensory motor cortex. It reflects the synchronous firing of motor neurons in rest state. Mu suppression is thought to reflect motor mirror neuron systems. Deficits in Mu suppression, and thus in motor neurons, play a role in autism. rTMS in the frequency band at the specific location will help normalize the mirror neurons to treat autism.

In a preferred embodiment of the present invention, an harmonic of a patient's heart rate is used to determine the rTMS frequency in a patient where the alpha brain wave frequency cannot be determined or which is poorly defined. An harmonic of the heart rate is chosen which most closely corresponds to a frequency within the alpha brain wave intrinsic frequency of 8-13 Hz. If the intrinsic alpha brain wave frequency of an autistic patient or an Alzheimer's patient cannot be determined or is ill-defined then an harmonic of the heart rate is chosen which is within the 8-13 Hz range. The patient is then treated with rTMS at that harmonic and the patient is monitored with EEG to determine when an intrinsic alpha brain wave frequency emerges. Then the rTMS frequency can be changed to this frequency if it is different than the original harmonic used. For example, if an autistic patient has a heart rate of 1.5 Hz and the patient's intrinsic alpha brain waves cannot be determined then the rTMS treatments are initially set to the $6^{th}$ harmonic or 9 Hz. The patient is treated at this frequency until an intrinsic alpha brain wave frequency is established. rTMS treatments are then continued at the intrinsic frequency.

The following Table 1 shows examples of the present invention where rTMS is used to modify alpha brain waves (intrinsic frequency 8-13 Hz). Table 1 shows the heart rate, the heart frequency in Hz and a frequency of the rTMS treatment. Typically the rTMS output intensity used to treat a patient is from 10% to about 120% of the motor threshold of the patient.

TABLE 1

| Heart Rate (beat/min) | Heart Rate in Hz | rTMS Frequncy in Hz |
|---|---|---|
| 50 | 0.83 | 9.96 |
| 60 | 1.0 | 9.0 |
| 65 | 1.08 | 8.64 |
| 70 | 1.17 | 11.7 |
| 75 | 1.25 | 11.25 |
| 80 | 1.33 | 10.64 |
| 85 | 1.42 | 11.36 |
| 90 | 1.5 | 9.0 |

The following Table 2 shows examples of the present invention where rTMS is used to modify delta brain waves (intrinsic frequency <4 Hz). Table 2 shows the heart rate, the heart frequency in Hz and a frequency of the rTMS treatment. Typically the rTMS power used to treat a patient is from 10% to about 120% of the motor threshold of the patient.

TABLE 2

| Heart Rate (beat/min) | Heart Rate in Hz | rTMS Frequncy in Hz |
|---|---|---|
| 50 | 0.83 | 2.49 |
| 60 | 1.0 | 3.0 |
| 65 | 1.08 | 2.16 |
| 70 | 1.17 | 3.51 |
| 75 | 1.25 | 2.50 |
| 80 | 1.33 | 2.66 |
| 85 | 1.42 | 2.84 |
| 90 | 1.5 | 3.0 |

The following Table 3 shows examples of the present invention where rTMS is used to modify theta brain waves (intrinsic frequency 4-8 Hz). Table 3 shows the heart rate, the heart frequency in Hz and a frequency of the rTMS treatment. Typically the rTMS power used to treat a patient is from 10% to about 120% of the motor threshold of the patient.

TABLE 3

| Heart Rate (beat/min) | Heart Rate in Hz | rTMS Frequncy in Hz |
|---|---|---|
| 50 | 0.83 | 4.98 |
| 60 | 1.0 | 6.0 |
| 65 | 1.08 | 7.56 |
| 70 | 1.17 | 5.85 |
| 75 | 1.25 | 5.0 |
| 80 | 1.33 | 6.65 |
| 85 | 1.42 | 4.26 |
| 90 | 1.5 | 4.5 |

The following Table 4 shows examples of the present invention where rTMS is used to modify beta brain waves (intrinsic frequency 13-30 Hz). Table 4 shows the heart rate, the heart frequency in Hz and a frequency of the rTMS treatment. Typically the rTMS power used to treat a patient is from 10% to about 120% of the motor threshold of the patient.

TABLE 4

| Heart Rate (beat/min) | Heart Rate in Hz | rTMS Frequncy in Hz (85% of Motor Threshhold) |
|---|---|---|
| 50 | 0.83 | 20.7 |
| 60 | 1.0 | 32.0 |
| 65 | 1.08 | 19.44 |
| 70 | 1.17 | 32.76 |
| 75 | 1.25 | 25.0 |
| 80 | 1.33 | 15.96 |
| 85 | 1.42 | 31.24 |
| 90 | 1.5 | 30.0 |

The following Table 5 shows examples of the present invention where rTMS is used to modify gamma waves (intrinsic frequency ~40 Hz). Table 5 shows the heart rate, the heart frequency in Hz and a frequency of the rTMS treatment. Typically the rTMS power used to treat a patient is from 10% to about 120% of the motor threshold of the patient.

TABLE 5

| Heart Rate (beat/min) | Heart Rate in Hz | rTMS Frequncy in Hz |
|---|---|---|
| 50 | 0.83 | 41.5 |
| 60 | 1.0 | 54 |
| 65 | 1.08 | 75.6 |
| 70 | 1.17 | 70.2 |
| 75 | 1.25 | 50.0 |
| 80 | 1.33 | 62.51 |
| 85 | 1.42 | 71.0 |
| 90 | 1.5 | 58.5 |

The following Table 6 shows examples of the present invention where rTMS is used to modify Mu brain waves of the sensory motor cortex (intrinsic frequency 8-13 Hz). Table 6 shows the heart rate, the heart frequency in Hz and a frequency of the rTMS treatment. Typically the rTMS power used to treat a patient is from 10% to about 120% of the motor threshold of the patient.

TABLE 6

| Heart Rate (beat/min) | Heart Rate in Hz | rTMS Frequncy in Hz |
|---|---|---|
| 50 | 0.83 | 9.13 |
| 60 | 1.0 | 10.00 |
| 65 | 1.08 | 8.64 |
| 70 | 1.17 | 11.7 |
| 75 | 1.25 | 12.5 |
| 80 | 1.33 | 10.64 |
| 85 | 1.42 | 8.52 |
| 90 | 1.5 | 10.5 |

The following example illustrates the practice of the present invention but should not be construed as limiting its scope.

Example 1

Treatment of Autism

A 9 year-old boy suffered from development delay in cognitive and fine motor functions, and had been diagnosed with autism. During the initial interview, the patient appeared to be slow in response to simple questions, exhibited a limited working memory and had obvious difficulty in writing and other fine motor functions. The patient was reported to have frequent head drops and improper gazing. He had been treated with anticonvulsants and was taking anticonvulsant medications. The patient's EEG showed diffused and left-frontal lobe dominant slow waves at 6.3 Hz with occasional short bursts of alpha rhythm in the occipital area but no clear and consistent intrinsic alpha frequency could be identified. Single-lead ECG showed a regular heartbeat at 1.5 Hz. Taking its $6^{th}$ higher harmonic, it was decided to set the rTMS at 9.0 Hz over the mid-central and left frontal lobe. Following the first 2 sessions of rTMS, the patient showed some degree of improvement with more vigilance and spontaneous communication. With further treatments there was a significant reduction of the slow waves in the patient's EEG and an increase in alpha rhythm. Clinically, the frequency of seizure episodes reduced significantly. After titrating down the anticonvulsant dosage over time, the patient experienced a significant improvement in cognitive and motor functions.

Example 2

Pain Relief—Pain Management

An adult male had chronic pain for several years after going through many back surgeries. The patient's EEG showed desynchronized alpha waves and a low alpha wave value. Single-lead ECG showed a regular heartbeat at 1 Hz. Taking its 9$^{th}$ higher harmonic, it was decided to set the rTMS at 9 Hz over the bilateral pre-frontal lobe. Following 3 sessions of rTMS, the patient showed a significant reduction in pain. The EEG pattern showed significant improvement in alpha synchronization.

Example 3

Treatment of Alzheimer's Disease

An adult female (85 years old) had been diagnosed with Alzheimer's disease for about 15 years. The patient's EEG showed alpha peak frequency below 8 Hz which is in the theta band range. Single-lead ECG showed a regular heartbeat at 1.2 Hz. Taking its 7$^{th}$ higher harmonic, it was decided to set the rTMS at 8.4 Hz over the bilateral pre-frontal lobe. Following 1 session of rTMS, the patient showed a significant improvement in short term memory and working memory. After 2 weeks of daily (Monday-Friday) rTMS sessions the patient became more coherent and her MMSE score improved from 14 pre-treatment to 21 post treatment. The EEG pattern showed an alpha wave near 8 Hz.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. A method of modulating a brain activity of a mammal wherein said method comprises subjecting the mammal to repetitive transcranial magnetic stimulation (rTMS) at a frequency of a non-EEG biological metric, or a harmonic or sub-harmonic of said non-EEG biological metric, for a time sufficient to modulate said brain activity and wherein an improvement in a physiological condition or a neuropsychiatric condition is achieved.

2. The method of claim 1 wherein the biological metric is heart rate, respiratory rate, or gastrointestinal movement rate.

3. The method of claim 1 wherein the brain activity is a desired EEG band and the rTMS frequency is equal to, or a harmonic or sub-harmonic of, a non-EEG biological metric that is closest to the targeted frequency in the desired EEG band.

4. The method of claim 3 wherein the non-EEG biological metric is heart rate.

5. The method of claim 1 wherein the physiological condition is concentration, sleep, alertness, memory, blood pressure, stress, libido, speech, motor function, physical performance, cognitive function, intelligence, height or weight.

6. The method of claim 1 wherein the neuropsychiatric condition is Autism Spectrum Disorder (ASD), Alzheimer's disease, ADHD, schizophrenia, anxiety, depression, coma, Parkinson's disease, substance abuse, bipolar disorder, a sleep disorder, an eating disorder, tinnitus, traumatic brain injury, post-traumatic stress syndrome, or fibromyalgia.

7. The method of claim 2 wherein the frequency is delta band (<4 Hz), theta band (4-8 Hz), alpha band (8-13 Hz), beta band (13-30 Hz), gamma band (~40 Hz) or Mu band (8-13 Hz).

8. A method of modulating a brain activity of a patient having Alzheimer's disease, wherein said method comprises subjecting the patient to repetitive transcranial magnetic stimulation (rTMS) at a frequency of a non-EEG biological metric, or a harmonic of said non-EEG biological metric, for a time sufficient to modulate said brain activity wherein an improvement in the symptoms of the Alzheimer's disease is achieved.

9. The method of claim 8 wherein the biological metric is the patient's resting heart rate.

10. A method of modulating a brain activity of a patient having chronic pain, wherein said method comprises subjecting the patient to repetitive transcranial magnetic stimulation (rTMS) at a frequency of a non-EEG biological metric, or a harmonic of said non-EEG biological metric, for a time sufficient to modulate said brain activity wherein an improvement in chronic pain is achieved.

11. The method of claim 10 wherein the biological metric is the patient's resting heart rate.

* * * * *